(12) United States Patent
Lee et al.

(10) Patent No.: US 6,920,360 B2
(45) Date of Patent: Jul. 19, 2005

(54) LARGE-SCALE PROCESSING LOOP FOR IMPLANTABLE MEDICAL DEVICES

(75) Inventors: Michael Thomas Lee, Minnetonka, MN (US); Nancy Perry Pool, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/740,080

(22) Filed: Dec. 18, 2000

(65) Prior Publication Data

US 2001/0039375 A1 Nov. 8, 2001

Related U.S. Application Data

(60) Provisional application No. 60/173,083, filed on Dec. 24, 1999, provisional application No. 60/173,082, filed on Dec. 24, 1999, provisional application No. 60/173,080, filed on Dec. 24, 1999, provisional application No. 60/173,079, filed on Dec. 24, 1999, provisional application No. 60/173,071, filed on Dec. 24, 1999, provisional application No. 60/173,065, filed on Dec. 24, 1999, provisional application No. 60/173,064, filed on Dec. 24, 1999, provisional application No. 60/173,062, filed on Dec. 24, 1999, provisional application No. 60/173,081, filed on Dec. 24, 1999, and provisional application No. 60/172,937, filed on Dec. 21, 1999.

(51) Int. Cl.[7] ................................................ A61N 1/08
(52) U.S. Cl. .......................... 607/60; 607/30; 128/903
(58) Field of Search ............................ 607/60, 32, 59, 607/30; 128/903, 904

(56) References Cited

U.S. PATENT DOCUMENTS

| | | | |
|---|---|---|---|
| 5,113,869 A | 5/1992 | Nappholz et al. | 128/696 |
| 5,186,170 A * | 2/1993 | Varrichio et al. | 607/45 |
| 5,348,008 A | 9/1994 | Bornn et al. | 128/642 |
| 5,720,770 A | 2/1998 | Nappholz et al. | 607/30 |
| 5,899,931 A * | 5/1999 | Deschamp et al. | 607/60 |
| 6,250,309 B1 | 6/2001 | Krichen et al. | 128/899 |
| 6,312,378 B1 * | 11/2001 | Bardy | 600/300 |
| 6,402,689 B1 * | 6/2002 | Scarantino | 600/300 |

FOREIGN PATENT DOCUMENTS

WO    WO 97/09923    3/1997    ............ A61B/5/00

* cited by examiner

*Primary Examiner*—Angela D. Sykes
*Assistant Examiner*—Roderick Bradford
(74) *Attorney, Agent, or Firm*—Paul H. McDowall; Girma Wolde-Michael

(57) ABSTRACT

A communication system is provided which permits of communication between a deployed implantable medical device (IMD) and a large-scale powerful computer capable of manipulating complex nonlinear modeling of physiologic systems, and also capable of accounting for large amounts of historical data from a particular patient or a cohort group for improved modeling and predictive power, which may be expected to lead to improved patient outcomes. A deployed IMD may be polled by a routing instrument external to the host patient, and data may be received by wireless communication. This data may be transmitted to a central large-scale or other relatively powerful computer for processing according to an appropriate model. A treatment or instruction regimen, as well as appropriate firmware or software upgrades, may then be transmitted to the routing instrument for immediate or eventual loading into the IMD via wireless communication.

17 Claims, 3 Drawing Sheets

LARGE-SCALE PROCESSING LOOP FOR IMPLANTABLE MEDICAL DEVICES

CROSS-REFERENCE TO RELATED APPLICATIONS

This application claims the benefit of U.S. Provisional Application No. 60/173,079, filed Dec. 24, 1999. The disclosure and drawings of the provisional application are specifically incorporated herein by reference.

FIELD OF THE INVENTION

The invention generally relates to implantable medical devices (IMDs). Specifically, the invention relates to a large-scale processing loop based on high resolution diagnostic/physiologic data collected by the IMDs. More specifically, the data collected by the IMDs is transferred to a remote computation center where evaluation and analysis is performed by high-speed computer resources. In the event a change, modification or reprogramming of the IMDs is indicated, the instruction is implemented in the IMDs at the next connection point in time, thus providing continuous monitoring to proactively effect changes in the IMDs for efficient therapy and clinical care, in contrast to responding to an adverse patient event or subjecting the patient and clinician to the inconvenience of frequent in-person encounters.

BACKGROUND OF THE INVENTION

The present invention is compatible and complementary with the elements disclosed in the following pending applications: "Medical System Having Improved Telemetry," filed Jul. 19, 1999, Ser. No. 09/356,340; "System and Method for Transferring Information Relating to an Implantable Medical Device to a Remote Location," filed on Jul. 21, 1999, Ser. No. 09/358,081; "Apparatus and Method for Remote Troubleshooting, Maintenance and Upgrade of Implantable Device Systems," filed on Oct. 26, 1999, Ser. No. 09/426,741; "Tactile Feedback for Indicating Validity of Communication Link with an Implantable Medical Device," filed Oct. 29, 1999, Ser. No. 09/430,708; "Apparatus and Method for Automated Invoicing of Medical Device Systems," filed Oct. 29, 1999, Ser. No. 09/429; "Apparatus and Method for Remote Self-Identification of Components in Medical Device Systems," filed Oct. 29, 1999, Ser. No. 09/429,956; "Apparatus and Method to Automate Remote Software Updates of Medical Device Systems," filed Oct. 29, 1999, Ser. No. 09/429,960; "Method and Apparatus to Secure Data Transfer From Medical Device Systems," filed Nov. 2, 1999, Ser. No 09/431,881 "Implantable Medical Device Programming Apparatus Having An Auxiliary Component Storage Compartment," filed Nov. 4, 1999, Ser. No. 091433,477; "Remote Delivery Of Software-Based Training For Implantable Medical Device Systems," filed Nov. 10, 1999, Ser. No. 09/437,615; "Apparatus and Method for Remote Therapy and Diagnosis in Medical Devices Via Interface Systems," filed Dec. 14, 1999, Ser. No. 09/460, 580; "Virtual Remote Monitor, Alert, Diagnostics and Programming For Implantable Medical Device Systems" filed Dec. 17, 1999, Ser. No. 09/466,284; "Instrumentation and Software for Remote Monitoring and Programming of Implantable Medical Devices (IMDs), filed Dec. 21, 1999, Ser. No. 60/172,937; "Application Proxy For Telecommunication-enabled Remote Medical Access Instruments," filed Dec. 4, 1999, Ser. No. 60/173,081; "Information Network Scheme For Interrogation Of Implantable Medical Devices (IMDs)," filed Dec. 24, 1999, Ser. No. 60/173,064; "Medical Device GUI For Cardiac Electrophysiology Display And Data Communications," filed Dec. 24, 1999, Ser. No. 60/173,065; "Integrated Software System For Implantable Medical Device Installation And Management," filed Dec. 24, 1999, Ser. No. 60/173, 082; "Dynamic Bandwidth Monitor And Adjuster For Remote Communications With A Medical Device," filed Dec. 24, 1999, Ser. No. 60/173,083 "Large-Scale Processing Loop For Implantable Medical Devices (IMDs)," filed Dec. 24,1999, Ser. No. 60/173,079; "Chronic Real-Time Information Management Systems For Implantable Medical Devices (LMDs)," filed Dec. 24,1999, Ser. No. 60/173,062; "Automatic Voice and Data Recognition For Medical Device Instrument Systems," filed Dec. 24, 1999, Ser. No. 60/173,071 "Central Switchboard to Facilitate Remote Collaboration With Medical Instruments," filed Dec. 24, 1999, Ser. No. 60/173,080; which are all incorporated by reference herein in their entireties.

In the traditional provision of any medical services, including routine check-ups and monitoring, a patient is required to physically present themselves at a provider's office or other clinical setting. In emergency situations, health care providers may travel to a patient's location, typically to provide stabilization during transport to a clinical setting, e.g., an emergency room. In some medical treatment applications, accepted medical practice for many procedures will naturally dictate physical proximity of medical providers and patients. However, the physical transport of patients to clinical settings requires logistical planning such as transportation, appointments, and dealing with cancellations and other scheduling complications. As a result of such logistical complications, patient compliance and clinician efficiency may suffer. In certain situations, delays caused by patient transport or scheduling may result in attendant delays in detection of medical conditions such as life-threatening situations. It is desirable, therefore, to minimize situations in which the physical transport of a patient to a clinical setting is required. It may also be desirable to minimize the extent to which an patient or patient information must be considered by a clinician at a particular time, i.e. during an appointment.

After the implantation of an IMD, for example, a cardiac pacemaker, clinician involvement with respect to the IMD has typically only begun. The IMD usually cannot be merely implanted and forgotten, but must be monitored for optimal results, and may require adjustment of certain parameters or settings, or even replacement, in response to or in anticipation of changes in patient condition or other environmental factors, or based on factors internal to the device. IMDs may also contain logic devices such as digital controllers, which may need to undergo firmware or software upgrades or modifications. In addition, information about the IMD may be gathered for treatment or research purposes. For example, many IMDs are capable of storing certain state information or other data regarding their operation internally.

While some data regarding IMD operation may be stored internally to the device, human physiological systems are very complex and nonlinear, i.e., exhibiting effects that may appear surprising or chaotic based on predictions using simple periodic or linear models. IMDs are designed to dynamically interact with these physiological systems on the fly, but often can only work with simplified models or the most elemental of the systems. The limitations of IMDs in interacting with physiological systems are twofold: There may be an incomplete understanding of the characteristics of the physiological system in all of its nonlinear complexity. However, there may be simply a lack of raw computing power on the part of the IMD.

Despite the limitations of IMDs with regard to processing power, IMDs are in a unique position to monitor physiological systems continuously. High-resolution data can be collected, but implantable devices may only store and process limited amounts of complex physiological and medical data.

Computing power (processor capability, memory, and adequate power supply) is abundantly available in the non-implantable ("external") world. The computing industry is still following Moore's Law (stating that transistor density will double every 18 months), delivering increasingly sophisticated computing devices yearly, and some of these gains accrue to the computer power of IMDs. However, frequent upgrading and replacement of IMDs based on more powerful models subjects a patient to additional stresses, and additional costs are imposed on the patient or health care system.

Models of physiological systems researched and developed on powerful external computing systems are often valuable in the medical world, but are not suitable for use in implantable medical devices. Cases involving long-term monitoring or forecasting are particularly well suited to external computing systems. External systems can deal with the complexity and amount of data, but because of their size, are of course not suitable for implantation.

Prior art methods of clinical services, particularly IMD monitoring and adjustment, are generally limited to in-hospital procedures or other scenarios involving patient transportation to a clinical setting. For example, if a physician needs to review the performance parameters of an IMD in a patient, it is likely that the patient has to go to the clinic. Further, if the medical conditions of a patient with an IMD warrant a continuous monitoring or adjustment of the device, the patient would have to stay in a hospital indefinitely. Such a continued treatment plan poses both economic and social problems. Under the prior art, as the segment of the population with IMDs increases, many more hospitals and clinics, and attendant clinicians and service personnel will be needed to provide in-hospital service for the patients, thus escalating the cost of healthcare. Additionally, the patients will be unduly restricted and inconvenienced by the need to either stay in the hospital or make very frequent visits to a clinic.

Yet another condition of the prior art practice requires that a patient visit a clinic center for occasional retrieval of data from the implanted device to assess the operations of the device and gather patient history for both clinical and research purposes. Such data is acquired by having the patient in a hospital/clinic to download the stored data from the IMD. Depending on the frequency of data collection, this procedure may pose serious difficulty and inconvenience for patients who live in rural areas or have limited mobility. Similarly, in the event a need arises to upgrade the software of an implantable medical device, the patient will be required to come into the clinic or hospital to have the upgrade installed.

Further, it is a typical medical practice to keep an accurate record of past and contemporaneous procedures relating to an IMD uplink with, for example, an IMD programmer, i.e. a computer capable of making changes to the firmware or software of an IMD. It is typically desired that the report contain the identification of all the medical devices involved in any interactive procedure. Specifically, all peripheral and major devices that are used in downlinking to the IMD may be reported. Currently, such procedures are manually reported, and require an operator or a medical person to manually enter data during each procedure. One of the limitations of such manual reporting procedures is the possibility for human error in data entry, thus motivating rechecking of the data to verify accuracy. Generally, the use of human clinicians to analyze data and implement changes in device therapy can result in inefficiencies and errors.

Yet a further condition of the prior art relates to the interface between a human operator and a programmer system. Generally, a medical device manager/technician, should be trained on the clinical and operational aspects of the programmer. Under current practices, an operator may attend a class/session sponsored by a clinic, hospital, or the manufacturer to successfully manage a programmer-IMD procedure. Further, the operator will preferably keep abreast of new developments and new procedures in the management, maintenance and upgrade of the IMD. Accordingly, it is desirable that operators of programmers, IMDs, and related medical devices receive regular training or information about the IMDs they work with. This information will preferably be widely distributed, because IMDs, programmers and related medical devices are distributed throughout the world. Further, the number of people having implanted medical devices has been increasing over the last few years, with an attendant increase in operator personnel. The total effect of these developments is a widely dispersed and large body of operators. Thus, it is desirable to have a high efficiency communications system that would enhance data communications, both between the IMDs and medical instruments, such as programmers; and between operators and entities providing IMD updates and education such as manufacturers.

A further limitation of the prior art relates to the management of multiple medical devices in a single patient. Advances in modern patient therapy and treatment have made it possible to implant a number of devices in a patient. For example, IMDs such as a defibrillator or a pacer, a neural implant, a drug pump, a separate physiologic monitor and various other IMDs may be implanted in a single patient. To successfully manage the operations and assess the performance of each device in a patient with multi-implants requires a continuous update and monitoring of the devices.

Further, it may be preferred to have an operable communication between the various implants to provide a coordinated clinical therapy to the patient. Thus, there is a need to monitor the IMDs and the programmer on a regular, if not a continuous, basis to ensure optimal patient care. In the absence of other alternatives, this imposes a great burden on the patient if a hospital or clinic is the only center where the necessary upgrade, follow up, evaluation and adjustment of the IMDs could be made. Further, even if feasible, the situation would require the establishment of multiple service areas or clinic centers to support the burgeoning number of multi-implant patients worldwide.

Generally, IMDs of the prior art are limited in that the features and functions of implantable medical device may not take full advantage of the complex modeling of physiologic systems that are being continually established; these devices simply lack the processing power to perform the required calculations, and may be expected to lack this power indefinitely. Accordingly, mankind's ever-increasing knowledge of physiologic systems must be simplified considerably in order to be implemented within an IMD. It would be desirable to provide a system by which the complex modeling of physiologic systems could be brought to bear in IMD instruction in order to improve patient outcomes.

SUMMARY OF THE INVENTION

This invention proposes to link the power of the external computing world to the implantable medical device via a network of communications devices.

A technology-based health care system that fully integrates the technical and social aspects of patient care and therapy will preferably flawlessly connect the client with care providers irrespective of separation distance or location of the participants.

Accordingly it is desirable to have a programmer unit that would connect to a centralized data source and repository. This may be termed, for example, a remote expert data center, a remote web-based data center, or a remote data center. This remote data center will preferably provide access to an expert system allowing for downloading of upgrade data or other information to a local environment. Further, it is important to have a large scale processing loop to enable the gathering of high resolution diagnostic/physiologic data, and to transfer information between the IMDs and a remote expert data center to dispense therapy and clinical care on real-time basis. Further, the large-scale processing loop contemplated by the present invention enables an efficient system for data storage, collection and processing to effect changes in control algorithms of the IMDs and associated medical units to promote real time therapy and clinical care.

The proliferation of patients with multi-implant medical devices worldwide has made it imperative to provide remote services to the IMDs and timely clinical care to the patient. The use of programmers and related devices to communicate with the IMDs and provide various remote services has become an important aspect of patient care. In addition to the instant invention, the use of programmers may be implemented in a manner consistent with the following co-pending applications assigned to the assignee of the instant invention: "System and Method for Transferring Information Relating to an Implantable Medical Device to a Remote Location," filed on Jul. 21, 1999, Ser. No. 09/358, 081; "Apparatus and Method for Remote Troubleshooting, Maintenance and Upgrade of Implantable Device Systems," filed on Oct. 26, 1999, Ser. No. 09/426,741; "Tactile Feedback for Indicating Validity of Communication Link with an Implantable Medical Device," filed Oct. 29, 1999, Ser. No. 09/430,708; "Apparatus and Method for Automated Invoicing of Medical Device Systems," filed Oct. 29, 1999, Ser. No. 09/430,208; "Apparatus and Method for Remote Self-Identification of Components in Medical Device Systems," filed Oct. 29, 1999, Ser. No. 09/429,956; "Apparatus and Method to Automate Remote Software Updates of Medical Device Systems," filed Oct. 29, 1999, Ser. No. 09/429,960; "Method and Apparatus to Secure Data Transfer From Medical Device Systems," filed Nov. 2, 1999, Ser. No. 09/431,881; "Implantable Medical Device Programming Apparatus Having An Auxiliary Component Storage Compartment," filed Nov. 4, 1999, Ser. No. 09/433,477; "Remote Delivery Of Software-Based Training For Implantable Medical Device Systems," filed Nov. 11, 1999, Ser. No. 09/460,580 "Apparatus and Method for Remote Therapy and Diagnosis in Medical Devices Via Interface Systems," filed Dec. 14, 1999, Ser. No. 09/466,284; "Virtual Remote Monitor, Alert, Diagnostics and Programming For Implantable Medical Device Systems" filed Dec. 17, 1999, Ser. No. 09/466,284; which are all incorporated by reference herein in their entirety. In light of the disclosures of these incorporated references, the present invention provides a vital system and method of delivering efficient therapy and clinical care to the patient.

In a representative embodiment of the instant invention, one or more IMDs, such as a pacemaker, defibrillator, drug pump, neurological stimulator, physiological signal recorder may be deployed in a patient. This IMD may be equipped with a radio frequency transmitter or receiver, or an alternate wireless communication telemetry technique or media which may travel through human tissue. For example, the IMD may contain a transmission device capable of transmitting through human tissue such as radio frequency telemetry, acoustic telemetry, or a transmission technique that uses patient tissue as a transmission medium. Alternately, an IMD may be deployed in a fashion by which a transmission or receiving device is visible externally to the patient but is connected directly or via wires to the IMD. An external device, which may generally be termed a routing instrument, may be positioned outside the patient, the routing device being equipped with a radio frequency or other communication means compatible with the communication media of the IMD or the IMD transmitter/receiver, which may be external to the IMD and may further be external to the patient. Communication may be effected between the IMD transmitter/receiver and the external routing instrument, e.g. via radio frequency. The routing instrument will be connected via a wireless or physical communication media e.g. via modem and direct dial connection, with a data network, LAN, WAN, wireless or infrared network. In an alternate embodiment of the subject invention, the routing instrument may have a direct connection or networked connection directly to the centralized computing resource. In yet another alternate embodiment of the subject invention, the system may be implemented as a data network that allows the routing instrument access to the computing center from many locations, for example providing for a routing instrument that is portable.

Using the computing power of external computing devices, and control systems using complex nonlinear analysis made possible by this computing power, the monitoring of long-term disease progression (e.g. heart failure, hypertension, diabetes) can be improved. Furthermore, therapies may be adjusted with finer granularity and improved results, with reduced need for human intervention and reduced opportunity for clinician error.

In addition to improved modeling of physiologic systems, the amount of historical data, particularly patient-specific historical data used as input to control systems can be virtually unlimited when it is stored externally to the patient. Furthermore, a more thorough comparison can be made between patients with similar diseases as data and therapy information, procedure and direction are centralized, which may be expected to result in gains to the body of medical knowledge and treatment efficacy. Data from other medical systems, either implanted or external, such as etiological databases, can be incorporated easily into the control system. Other anonymous patient experiences or treatment data may be more quickly incorporated into a subject patient's IMD regime than might be possible with existing systems of IMD programming or upgrading. In addition, a subject patient's own historical treatment parameters and corresponding outcomes may be used in making IMD programming and other treatment decisions.

The instant invention provides IMDs with access to virtually unlimited computing power as part of their data collection and therapy calculation processes. In an alternate embodiment of the present invention, the IMD may be used by an external computing device as a data collection agent, and as an agent to implement changes to a treatment regimen based on a complex dynamical or stochastic physiological model. Rather than continuously increasing the processing power of IMDs, the present invention provides a link with external computing power, which is more easily upgraded. In addition, control system algorithms based on current knowledge about physiologic systems could be more easily updated using a centralized powerful processor, rather than individually updating the firmware or software of thousands of deployed IMDs.

When multiple IMDs are deployed within a single patient, the data and therapy from these IMDs may be more easily and efficiently orchestrated, thus further improving treatment efficacy and convenience to the patient and clinician, and in some cases judiciously limiting clinician involvement. In addition, high resolution or finely grained data may be collected and stored from a vast number of subject IMDs. This finely grained patient data may be expected to prove valuable in defining and modifying an individual patient's treatment regimen as implemented by an IMD. In addition, this high-resolution data may be analyzed on a mass scale, providing opportunities for improvement of existing physiologic models. This data may serve, for example, to validate physiologic models being employed, or may suggest refinement of these models based on numerous patient outcomes.

This refinement of therapy and diagnostic algorithms or models may further be refined in conjunction with external medical devices as well. According to the present invention, IMD management and manipulation will be more efficient and efficacious. For example, an embodiment of the present invention permits the use of complex control systems to manage therapy of implantable medical devices. In addition, the invention permits the orchestration of the data collection and therapy functions of IMDs, particularly the functions of multiple IMDs implanted in one patient. In addition, an embodiment of the present invention permits of centralized therapy prescription, and provides the ability to compare disease states, diagnostic data and therapy prescription across patients with fine granularity. The ability to update control system software and hardware at a central location is also provided, as well as the ability to upgrade the firmware or software in remotely distributed, deployed IMDs from one central location.

A communications system according to the present invention provides the ability to have high-power computing systems interact with implanted medical devices, thus providing the ability to use complex control algorithms and models in implanted medical devices. In addition, even with relatively simple modeling, or in stochastic models, relatively large amounts of historical data from a single or multiple medical devices may be brought to bear for predictive purposes in evaluating alternate therapy and IMD instruction prescriptions. The present invention provides a system that establishes an external communications device and data network as a 'data bus' for extending the processing power of deployed IMDs, while minimizing host patient and clinician inconvenience.

DETAILED DESCRIPTION OF THE DRAWINGS

Figure 1:
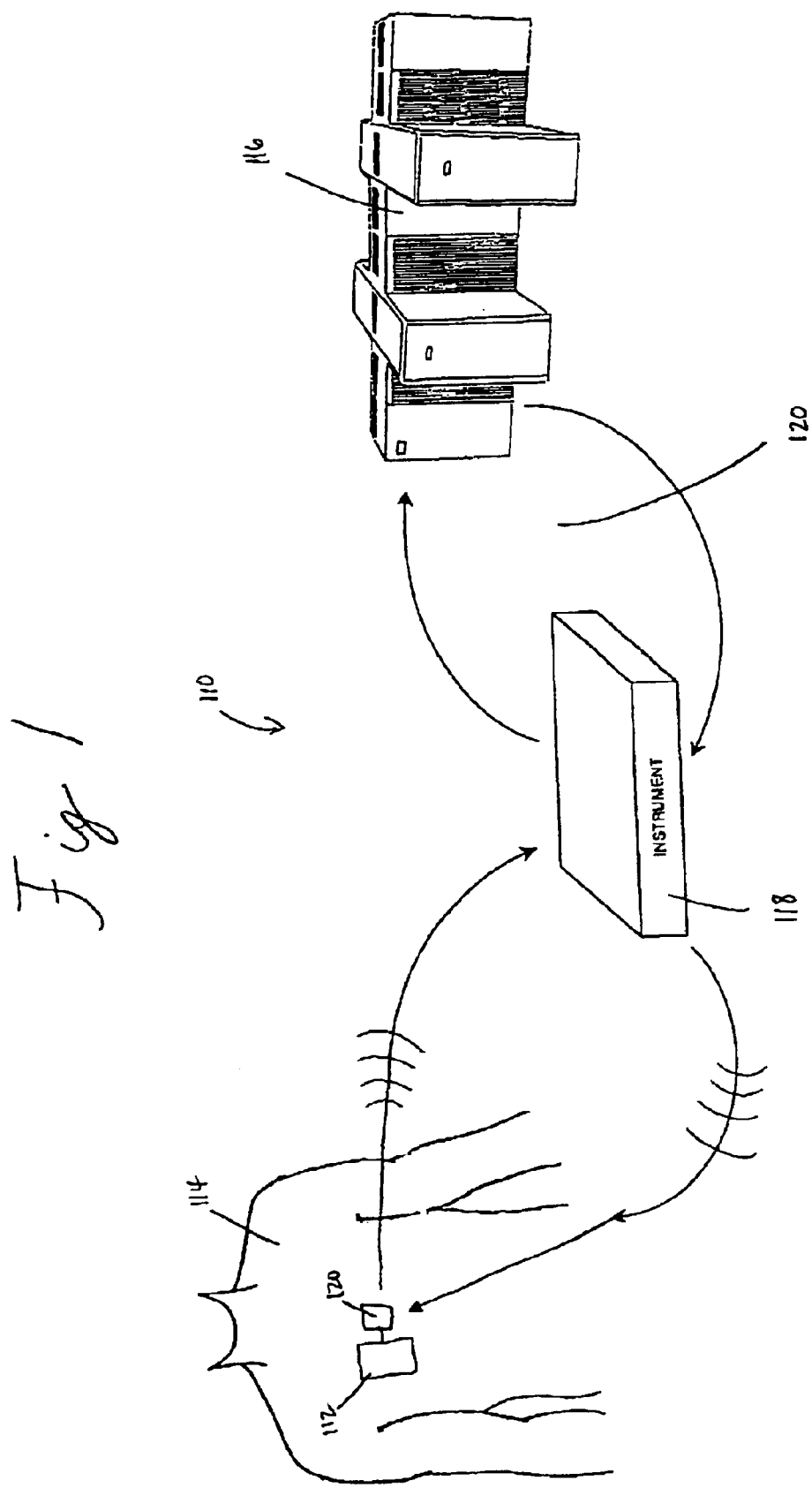
FIG. 1 depicts a general network architecture diagram of system embodying the subject invention.

FIG. 1 depicts a general architectural view of a large-scale processing network according to an embodiment of the present invention. An IMD programming and instruction system 110 is provided. IMD 112 has been deployed in a patient 114, for example, a patient at a location remote from large-scale processor 116. The IMD may be one of a number of existing or to be developed IMDs, for example, a pacemaker, defibrillator, drug pump, neurological stimulator, physiological signal recorder, oxygen sensor, or the like. While in FIG. 1, a single IMD 112 is depicted, the subject invention permits of use with multiple IMDs deployed in a single patient, each making separate transmissions and receiving separate instructions from routing instrument 118. In an alternate embodiment of the subject invention, multiple IMDs deployed in a single patient are all linked to a single telemetry device implanted in a patient. This telemetry device may be separate from or incorporated into one of the IMDs deployed in a patient.

Returning to the single IMD embodiment depicted in FIG. 1, IMD 112 is equipped with or linked to a transmission and receiving device such as a radio frequency telemetry device 120, also implanted in patient 114. In a preferred embodiment of the subject invention, an external device is provided which may be termed a routing instrument. This routing instrument 118 may communicate with the IMD via radio frequency, as discussed above. The routing device 118 may also communicate with a data network via modem, LAN, WAN, wireless or infrared means. This data network 120 is preferably able to communicate via a computer network or other suitable data communications connection with a central computer 116 capable of carrying out large scale or parallel processing of patient data from one or more patients having deployed IMDs. The large-scale computing center or central computer 116 preferably has sufficient computing power and storage capability to collect and process large amounts of physiological data using complex control systems. The patient is placed or places himself or herself in proximity to routing instrument 118. For example, routing instrument 118 may be placed in a patient's home, at their bedside perhaps, or may be placed in a community center, clinical office setting, nursing home, or other care facility. Routing instrument 118 may also be embodied in a portable device that may be carried by the patient while outside the home or traveling. Routing device 118, like IMD 112, contains or is linked to a communications media transmitter/receiver compatible with the type incorporated into or linked to IMD 112. In an illustrative embodiment of the subject invention, routing instrument 118 contains a radio frequency transmitter/receiver or similar radio frequency telemetry device.

In addition to communicating with IMD 112 as discussed above, routing instrument 118 may communicate with central large-scale computer 116 via a number of network schemes or connections, with regard to any of the OSI layers. For example, communication may be effected by way of a TCP/IP connection, particularly one using the Internet, as well as a LAN, WAN, MAN, direct dial-up connection, a dedicated line, or a dedicated terminal connection to a mainframe.

Large-scale computer 116 will preferably possess appreciably more computing power than possible with an IMD, in terms of processor speed, RAM available, and data storage. While computer 116 is referred to a large-scale, it is large scale only relative to such processors that are available for incorporation into an IMD. For example, some commercially-available personal computers may contain sufficient computing power to operate as a server capable of carrying out many IMD diagnostic and programming tasks. In a preferred embodiment of the subject invention, however, large-scale computer 116 will be a mainframe, multi-processor supercomputer, or a multi-processor workstation, such as a type available from Silicon Graphics, Inc./SGI of Mountain View, Calif. Such relatively high-powered computing devices are better suited to calculations involving nonlinear systems and models such as those being developed to model physiologic systems. Regardless of which computing device is used, in accordance with the present invention, the computing device will be configured as a server capable of communicating directly or indirectly with routing instrument 118. The computer 116 will preferably have sufficient storage, either internal to the computer or linked to the computer, for the storage of massive amounts of historical patient data from, for example, a particular patient having an IMD in communication with computer 116, and/or subject data from relevant physiologic studies or from cohort groups having similar medical conditions and/or deployed IMDs.

Security and integrity of the patient information will preferably be closely guarded for at least the following reasons: First, patient physiologic data detected by a deployed IMD will be transmitted via routing instrument 118 to computer 116 for purposes of analysis of this data, and treatment regimens and/or IMD instructions, firmware, or software may be changed on the basis of this information. Accordingly, integrity of transmitted data and instructions will preferably be maintained so as to avoid adverse patient outcomes or patient outcomes that do not take full advantage of the subject invention. In addition, patient information that may be linked to an identifiable individual is typically regarded as confidential. Accordingly, encryption will preferably be provided to ensure patient confidentiality, particularly when transmissions between routing instrument 118 and computer 116 takes place though media other than a dedicated line/direct dial-up connection, such as a packet based network technology over a public network or internetwork. For example, if the transmissions are routed over the Internet using TCP/IP, encryption will preferably be used. As an alternative to encryption, a proprietary data exchange format/interface that is kept secret may be used in communications between IMD 112 and computer 116. However, even with secure dedicated lines or a secret data format, digital signatures will preferably be used to detect corruption of data.

Accordingly, a preferred embodiment of the subject invention utilizes digital signatures and encryption of the patient information and IMD instructions being transmitted according to the present invention. Encryption of patient information will serve to protect patient confidentiality. Each transmission of patient data will preferably have a digital signature that can be checked against the transmission payload to ensure that patient data and IMD instructions were not corrupted during transmission. Examples of encryption/digital signature schemes that should prove sufficient Encryption of patient information and digital signatures include PGP, the RSA public key infrastructure scheme, or other consumer-level or higher, prime number based encryption signature scheme.

Transmissions between an IMD 112 and a routing device 118 will also preferably be protected from transmission errors using similar encryption, authentication, and verification techniques, and/or wireless communication enhancement techniques such as wireless modulation or another suitable wide-frequency spectra technique. Preferably, encryption and/or authentication will be effected end-to-end, i.e., covering the entire transmission from IMD 112 to computer 116 or from computer 116 to IMD 112, rather than effecting one encryption/verification scheme between IMD 112 and routing instrument 118, and a different scheme from routing instrument 118 and computer 116. As an alternative to, or in addition to the above authentication scheme, radio frequency pulse coding, spread spectrum, direct sequence, time-hopping, frequency hopping, a hybrid spread spectrum technique, or other wireless modulation techniques may be employed in order to reduce interference between IMD 112 and other IMD or other wireless devices, and to generally offer improved accuracy, reliability, and security to transmissions between IMD 112 and routing instrument 118, may be used to avoid cross-talk or confusion among IMDs and/or routing instruments in proximity to each other. For example, radio coding may be implemented to avoid transmission errors or device confusion between neighboring IMD patients utilizing a device embodying the present invention in a managed-care setting.

Preferably, a data network is provided that allows the external communications device, or routing instrument 118, access to the computing center from one of many possible locations. This provides portability to the administration of the routing instrument and patient lifestyle.

In operation, the deployed IMD collects physiological data from the host patient via electrical, mechanical or chemical sensors, according to the type of IMD deployed in the host patient. Some of this data may be used locally, i.e., processed and analyzed internally to the IMD itself, to modify therapy or treatment on a 'real-time' basis. Regardless of whether the physiological data from the host patient is used to modify therapy on this self-contained basis, the patient data will preferably be buffered in the IMD until such time as the device is polled or "interrogated" by routing instrument 118. This interrogation may take place in accordance with co-pending application of the common assignee, entitled "Implantable Medical Device Interrogation Network, Ser. No. 60/173,082", and filed on Dec. 24, 1999; this co-pending application is hereby incorporated by reference in its entirety into the instant application. During this transaction, the routing instrument 118 may also pass instructions received from the computing center to the IMD.

Routing instrument 118 may contact the computing center or central large-scale processor 116 and transmit the physiologic data uploaded from IMD 112 to routing instrument 118. The powerful computer(s) at the computing center 116 may store and/or process the data, perhaps combining it with historical data of the same type from the same device, or perhaps with data from other implanted and medical devices. For example, the physiologic data may be combined with anonymous data from other demographic or clinical groups consisting of subjects which may have data relevant or generalizable to host patient 114. For example, comparisons of the data collected may be made with data from other patients with similar disease states, and therapy solutions constructed and compared.

The computing center may then transfer instructions on modifications to therapy and data collection to the routing device 118. At the next opportunity for communications, the routing device transfers the instructions to the IMD and may also collect an additional batch of data buffered in the IMD. This opportunity for communication between routing device 118 and IMD 112 may not be immediately present. For example, host patient 114 may be located away from routing instrument temporarily, if the host patient has left their house or clinical setting where the routing device is kept. An alternate barrier to routing device to IMD communication may be a poor environment for the communication media employed between the IMD and the routing device 118.

Data may also be held at central computing center 116, for example, if the routing device 118 is carried by host patient 114 as a portable device, and an analog connection for a modem or suitable network connection may not be available.

In a preferred embodiment of the subject invention, communication system 110 will operate asynchronously, permitting for the possibility for breaks in the continuous and real-time communications and/or processing of the three subsystems (IMD 112, routing instrument 118, and large scale computer 116. However, alternate embodiments of the invention are also possible, including synchronous, "real-time" control of the target IMD 112. This alternate "real-time" embodiment of the system 110 may be enhanced upon the establishment of more ubiquitous and robust communications systems or links.

Initially the system would act in an asynchronous manner, where precise timing of data transfer and therapy changes is not critical. As the device-instrument and network communications become more ubiquitous and less reliant on specific hardware (e.g. RF head, network cables), the control loop could become more time-dependent.

Figure 2:
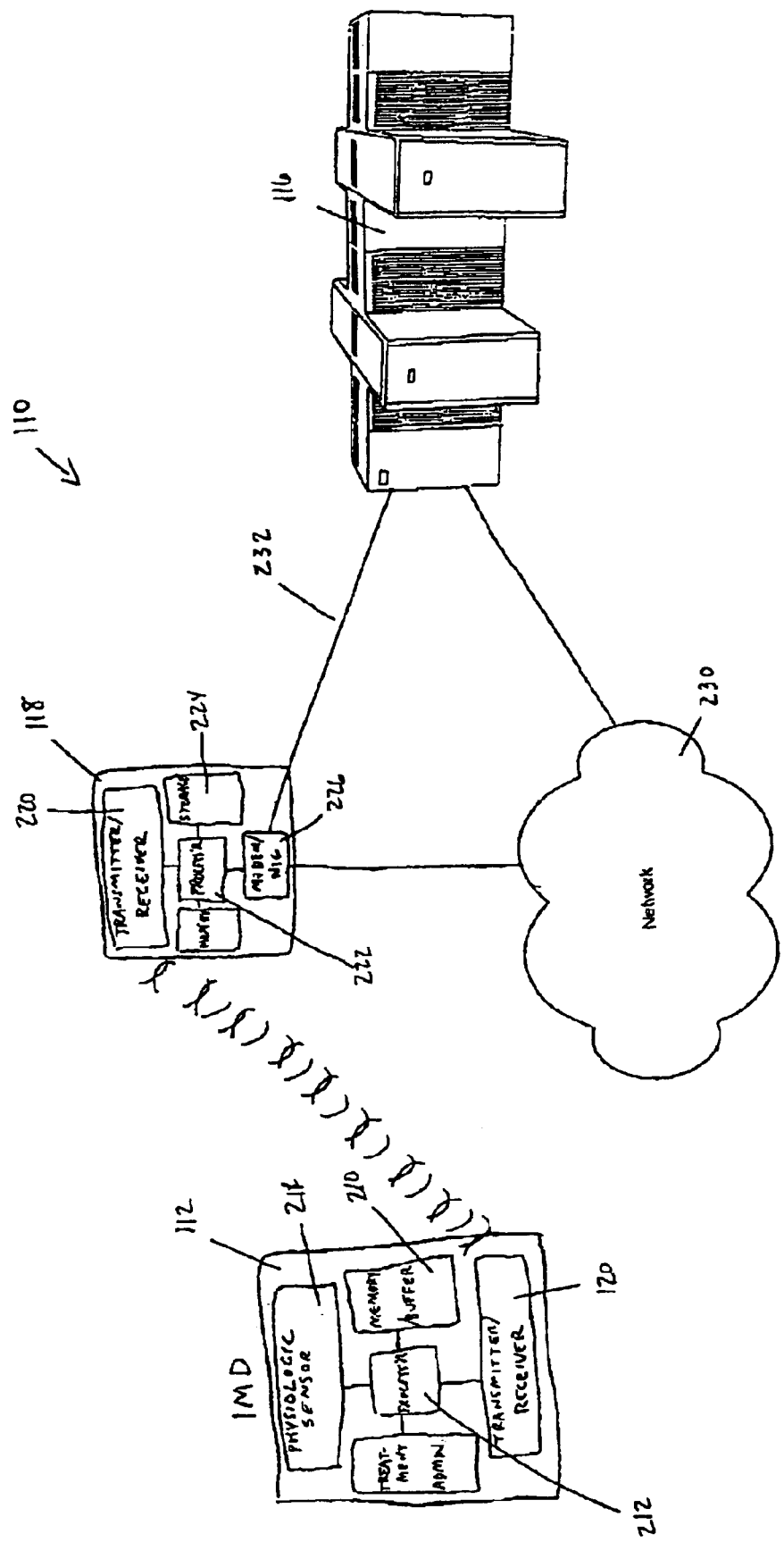
FIG. 2 depicts the system of FIG. 1 including specific functional modules within the components of the system.
Figure 3:
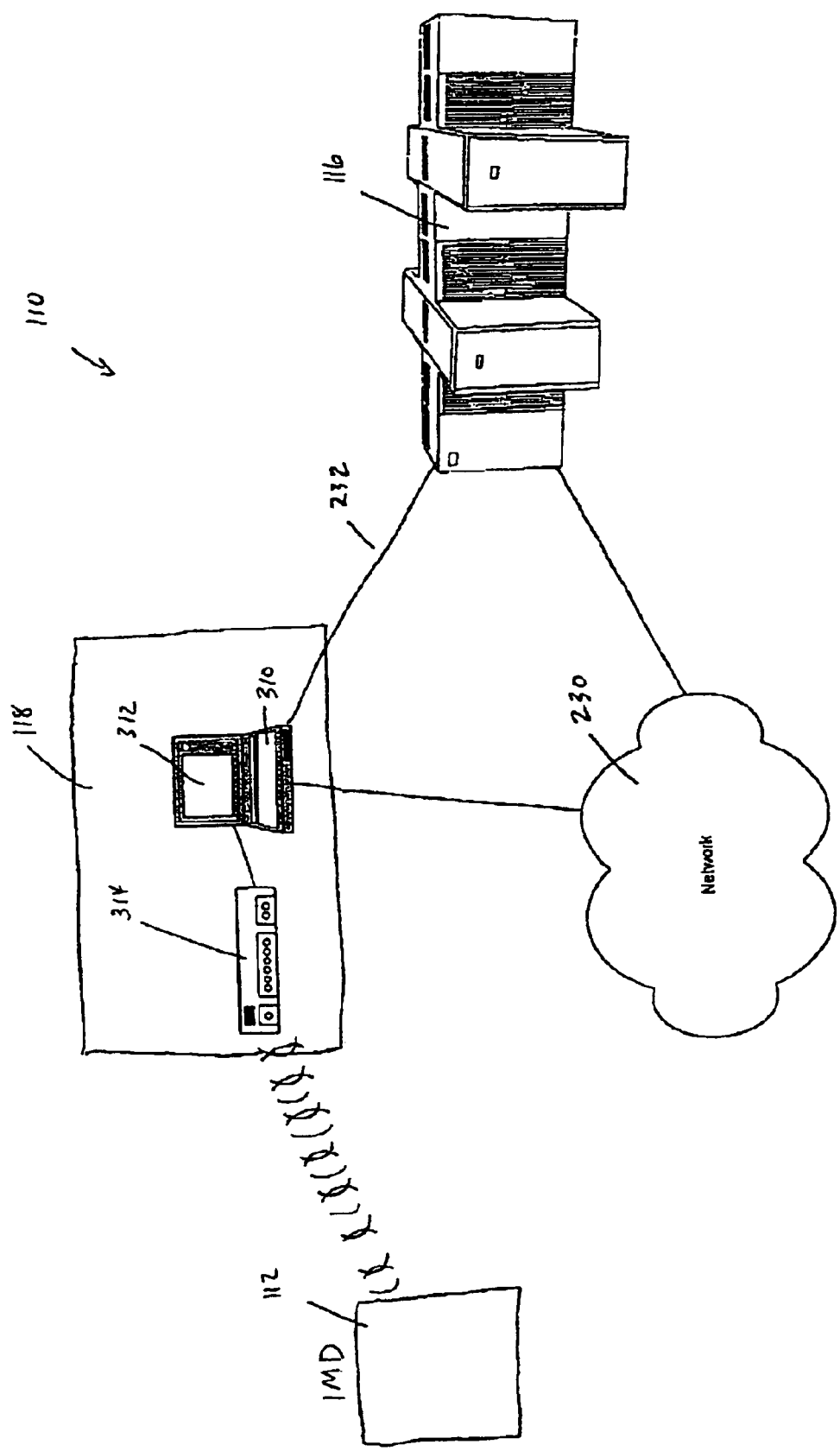
FIG. 3 depicts an alternate embodiment of the system depicted in FIG. 2.

In a preferred embodiment of the subject invention, and as depicted in FIG. 2, IMD 112 effects the collection of high resolution physiological data; and provides for its temporary storage or buffering, for example in storage device 210. This storage device is preferably a RAM module of a type suitable for implementation in IMDs. Prior to storage in storage device 210, IMD processor 212 will preferably compress the physiologic data collected by physiologic sensor 214. IMD processor 212, in addition to processing the reception and storage of physiologic data, also preferably effects implementation of IMD therapy. For example, and depending on the type of IMD in which the subject invention is implemented, processor 212 may control the amount or frequency of electrical stimuli or drug delivered by IMD 112. This control will preferably be based on instructions originating from central computer 116, after processing of relevant historical or patient cohort data and determination of a suitable treatment regimen that may be effected by IMD 112. FIG. 2 also depicts in greater detail the architecture of routing instrument 118 of FIG. 1. As shown in FIG. 2, routing instrument 118 contains a transmitter/receiver 220, a processor 222, storage device 224, and communication device 226. Communication device 226 may be, for example, a modem or network interface card. It may be seen in FIG. 2 that routing instrument 118 contains architecture components similar to those seen in a computer, and FIG. 3 depicts the communication system 110 of FIGS. 1 and 2 with routing instrument 118 implemented as a computer 310 with a peripheral device 314 that may communicate with IMD 112. As shown in FIG. 2, communications between routing instrument 118 and computing center 116 may be effected either through a network 230, such as a LAN or the Internet, or communications may be effected through a direct dial-up or dedicated line, or through a terminal connection to a mainframe. These possible implementations are indicated generally by communications link 232. Typically, these connections may be considered alternatives, or both communications links, i.e., relatively direct link 232 and link through network 230 may be implemented in order to provide a backup communications system to the link used as the primary communication method.

In a preferred embodiment of the subject invention depicted in FIG. 2, central computing center or computer 116 creates an instruction file for routing instrument 118 and/or for IMD. This file may consist largely of instructions for the IMD 112 affiliated with the routing device 118. Central computer 116 may then contact the routing instrument to initiate transfer. Preferably, this method of contact will correspond to the method of communication from routing instrument 118 to central computer 116, although an alternate method may be used, particularly if a first preferred method proves unsuccessful. If communication with routing device 118 is possible, suitable instructions or information may be forwarded to routing device 118 for communication to IMD 112. If both a primary and backup methods of communication prove unsuccessful, central computer 116 may leave for routing instrument 118 an instruction file that it may collect upon establishment of a connection.

While the instant invention has been described primarily with a single IMD corresponding to a single routing device and to a single central computer, alternative embodiments of the present invention are possible. For example, several IMDs, each with a separate identifying code or number, may utilize a single routing instrument. These several IMDs sharing a routing instrument may be deployed within a single patient, or the several IMDs sharing a routing instrument may be deployed in two or more separate patients, where each patient has reasonable access to the routing instrument directly or to communications equipment which may send information to and receive information from routing instrument 118. While in an illustrative embodiment, several routing instruments share a single central computing resource, alternative embodiments may have a single routing instrument communicating with distributed computers. In addition to or in place of large-scale computer 116. For example, a routing instrument 118 may submit physiologic data to one computer 116 for wide demographic or cohort analysis, or deep historical data about the patient whose treatment is being considered. A second central computer of relatively large scale may be used for formulating instructions to particular deployed IMDs. These instructions may be educated by or based on the outcome of a demographic analysis from the same or a different large-scale computer, or may be based on a nonlinear multivariate model resident on the large-scale computer. In addition, an instruction regimen for a target IMD may not be based solely on treatment considerations arising from patient data or from predictive modeling. IN addition, an instruction regimen may contain firmware or software upgrades to target IMD 112 which are prescribed generally for all host patients of a particular IMD model or type.

Upon establishing contact with routing instrument 118, an IMD instruction regimen may be pushed or generally transmitted to routing instrument 118, or computer 310 in FIG. 3 implementing the routing function. Routing instrument 118 or equivalent then stores the results of processing or analysis carried out by large-scale computer 116. The IMD instruction regimen prescribed by central computer 116 may be stored within routing device 118 indefinitely or for a fixed period of time prior to expiration. At the next opportunity for communication between routing device 118 and IMD 112, routing instrument provides new therapy programming, as well as new instructions for data collection if necessary. In a preferred embodiment of the subject invention, if an instruction regimen has been received by routing device 118 for communication to target IMD 112, routing device 118 will periodically poll IMD 112 in attempts to establish a communication link, such as a wireless link. In an alternate embodiment of the subject invention, routing device 118 may have a display feature, which could be for example an LCD display or a simple indicator light indicating that an instruction regimen has been received for forwarding from central computer 116. A human user, for example, host patient 114 of FIG. 1 may press a button or otherwise initiate the process of communication between routing device 118 and target IMD 112. If routing device 118 is implemented on a computer such as a PC 310 of FIG. 3 with a transmitter/receiver peripheral device, a suitable pop-up message on PC monitor 312 may indicate a pending IMD instruction or request, or an indicator on a display of peripheral transmitter/receiver 314 may indicate a pending instruction as above.

If an IMD instruction regimen has expired prior to establishment of contact with the target IMD 112, routing device may send an error message identifying the IMD and/or instruction regimen by a suitable code. Upon reception of an error in instruction regimen transmission, central computer 116 may be programmed to carry out suitable updating of an instruction regimen, or an error message may be output to a human operator or clinician for direct intervention by voice telephony or direct contact by mobile clinical personnel, for example.

While routing device 118 is portrayed in FIG. 2 as a self-contained or stand-alone unit, it will be appreciated that routing device 118 may also be implemented, as depicted in FIG. 3, as a peripheral transmitter receiver capable of wireless communication with IMD 112, and also in communication with computer 310, such as a personal computer such as a laptop or portable computer. Computer 310 may also be a terminal of a remote mainframe computer 116, at which large-scale computing tasks may be carried out. It will be appreciated that in the event that routing instrument 118 is implemented as a peripheral and mainframe terminal, some of the components of routing device 118, such as storage device 224, may be implemented on a mainframe computer 116 rather than in the terminal implementing routing device 118. In the embodiment of the invention depicted in FIG. 3, transmitter/receiver 314 serves merely as a communication interface between IMD 112 and routing computer 310. The functions of routing instrument 118 of FIG. 2 may be implemented in software resident on routing computer 310. Communications interfaces of routing computer 310 may include a modem, network card, direct connection, or terminal connection. In the embodiment of the invention depicted in FIG. 3, in which a IMD-local computer 310 carries out communication with large scale computer or mainframe 116, preferably all data communication security and message authentication and integrity confirmation as discussed above with regard to routing instrument 118 of FIG. 2 will be implemented on local computer 310 of FIG. 3. As discussed with reference to FIG. 2 above, communication between the computer 310 implementing routing instrument 118, and central computer 116 may be implemented via network 230 or direct connection 232.

Although the invention is described with reference to particular embodiments, it will be understood to those skilled in the art that this embodiment is merely illustrative of the application of the principles of the invention. Numerous modifications may be made therein and other arrangements may be devised without departing from the spirit and scope of the invention.

What is claimed is:

1. A method of computerized control of an implantable medical device deployed in a patient, comprising the steps of:
   providing a centralized computing resource external to a patient having a physiologic model;
   transmitting via a network communication link a set of historical physiologic data previously gathered from the implantable medical device to a centralized computing resource external to a patient;
   performing a computerized analysis of the transmitted Bet of historical physiologic data using the physiologic model that produces a set of results; and
   making a computerized determination of a set of instructions comprising an implantable medical device therapy regimen based at least in part on the set of results from the analysis of the set of historical physiologic data; and
   transmitting via the network communication link or a separate network communication link the set of instructions to the implantable medical device for execution by the implantable medical device in accordance with a firmware- or a software-implemented executable routine.

2. A method according to claim 1, wherein the network communication link or the separate network communication link comprises a radio frequency link, a hard-wired link, an infrared-band link, or other type of a wireless communication link.

3. A method according to claim 2, wherein the network communication link or the separate network communication link comprises a hybrid link.

4. A method according to claim 3 wherein the hybrid link comprises a radio frequency link from said implantable medical device to a routing instrument, and a secondary network link from the routing device to the central computing resource.

5. A method according to claim 4 wherein the secondary network link is an area network.

6. A method according to claim 5 wherein the area network is a large area network.

7. A method according to claim 5 wherein the area network comprises a wide area network.

8. A method according to claim 5 wherein the area network comprises at least one of an internet-, an intranet-, an extranet- or a world wide web-based network.

9. A method according to claim 4, wherein the secondary network communication link comprises an asynchronous link.

10. A method according to claim 4, wherein the secondary network communications link comprises a synchronous link.

11. A method according to claim 4, wherein the secondary network link is a direct dial up connection.

12. A method according to claim 1, wherein each of the two or more implantable medical devices comprises one or more of: a pacemaker, a pacemaker/cardioverter/defibrillator, a defibrillator, an oxygen sensing device, a nerve stimulator, a muscle stimulator, a drug pump, a neurological stimulator, a physiological signal recorder or an implantable monitoring device.

13. A computerized control system linking an implantable medical device deployed in a patient to a centralized external computer via a data communication network, said computerized control system providing computerized control of the implantable medical device deployed in the patient, comprising:
   a central computing resource accessible by the data communication network, said central computing resource including a physiologic model and being operable to (a) analyze a set of patient data recorded by the implantable medical device and transmitted via the data communication network using the physiologic model, and (b) make a computerized determination of a set of instructions comprising an implantable medical device therapy regimen based on the set of results from the analysis of the set of historical physiologic data;

at least one routing instrument capable of wireless communication with said implantable medical device deployed in a patient, said at least one routing instrument being capable of performing a data communication sequence with the data communication network.

14. A computerized information network according to claim 13, wherein the data communication network comprises a direct link between the at least one routing instrument and the central computing resource.

15. A computerized information network according to claim 13, wherein the central computing resource comprises a multi-processor workstation.

16. A computerized information network according to claim 13, wherein the central computing resource comprises a networked cluster of computers.

17. A computerized information network according to claim 13, wherein the data communication protocol comprises an asynchronous protocol.

* * * * *

UNITED STATES PATENT AND TRADEMARK OFFICE
CERTIFICATE OF CORRECTION

| | | |
|---|---|---|
| PATENT NO. | : 6,920,360 B2 | Page 1 of 1 |
| APPLICATION NO. | : 09/740080 | |
| DATED | : July 19, 2005 | |
| INVENTOR(S) | : Lee et al. | |

It is certified that error appears in the above-identified patent and that said Letters Patent is hereby corrected as shown below:

In column 14, lines 3-4, delete "Bet of historical" and insert therefore --set of historical--.

Signed and Sealed this

Ninth Day of January, 2007

JON W. DUDAS
*Director of the United States Patent and Trademark Office*